(12) United States Patent
Ratty et al.

(10) Patent No.: US 10,414,728 B2
(45) Date of Patent: Sep. 17, 2019

(54) USE OF TETRAHYDROPYRIDINES IN THE TREATMENT OF SODIUM CHANNEL RELATED DISEASE AND DISORDERS

(71) Applicant: CENNERV PHARMA (S) PTE. LTD., Singapore (SG)

(72) Inventors: Anil Kumar Ratty, Singapore (SG); Michael Entzeroth, Singapore (SG)

(73) Assignee: CENNERV PHARMA (S) PTE LTD, Singapore (SG)

( * ) Notice: Subject to any disclaimer, the term of this patent is extended or adjusted under 35 U.S.C. 154(b) by 0 days.

(21) Appl. No.: 15/522,510

(22) PCT Filed: Nov. 19, 2015

(86) PCT No.: PCT/SG2015/050461
§ 371 (c)(1),
(2) Date: Apr. 27, 2017

(87) PCT Pub. No.: WO2016/089304
PCT Pub. Date: Jun. 9, 2016

(65) Prior Publication Data
US 2017/0355676 A1 Dec. 14, 2017

(30) Foreign Application Priority Data
Dec. 5, 2014 (SG) .............. 10201408115S

(51) Int. Cl.
*C07D 211/70* (2006.01)
*A61K 31/4402* (2006.01)

(52) U.S. Cl.
CPC ........ *C07D 211/70* (2013.01); *A61K 31/4402* (2013.01)

(58) Field of Classification Search
USPC ........................................................ 514/277
See application file for complete search history.

(56) References Cited

U.S. PATENT DOCUMENTS

| 7,700,798 B1 * | 4/2010 | Davies ............... C07C 29/147 560/56 |
| 7,851,487 B2 * | 12/2010 | Davies ............... A61K 31/44 514/317 |
| 2007/0249646 A1 * | 10/2007 | Davies ............... A61K 31/44 514/277 |

FOREIGN PATENT DOCUMENTS

| WO | WO 00/64583 A1 | 11/2000 |
| WO | WO 2006/047330 A2 | 5/2006 |
| WO | WO 2006/078984 A2 | 7/2006 |
| WO | WO 2007/106508 A2 | 9/2007 |

OTHER PUBLICATIONS

International Search Report and Written Opinion dated Dec. 21, 2015 in connection with PCT/SG2015/050461.
Davies et al., Synthesis of methylphenidate analogues and their binding affinities at dopamine and serotonin transport sites. Bioorg Med Chem Lett. Apr. 5, 2004;14(7):1799-802.
Extended European Search Report and Search Opinion dated May 7, 2018 for Application No. EP15864987.1.
Aboul-Enein et al., Normal phase chiral HPLC of methylphenidate: comparison of different polysaccharide-based chiral stationary phases. Chirality. Jan. 2002;14(1):47-50.

* cited by examiner

*Primary Examiner* — Sabiha N Qazi
(74) *Attorney, Agent, or Firm* — Joseph G. Chu; JCIP

(57) ABSTRACT

The present invention provides a method of treating one or more sodium channel related diseases or disorders in an individual, including related symptoms. The method comprises administering to the individual a tetrahydropyridine derivative in an amount effective to treat sodium channel related diseases or disorders in individuals. These compounds are generally categorized as Ritalin related compounds. The present invention also provides compounds for use in the treatment of and also for use in the manufacture of a medicament for the treatment of sodium channel related diseases or disorders in an individual. A method is further provided for the preparation and isolation of the derivatives of the compound of the present invention.

3 Claims, 6 Drawing Sheets

Figure 1:
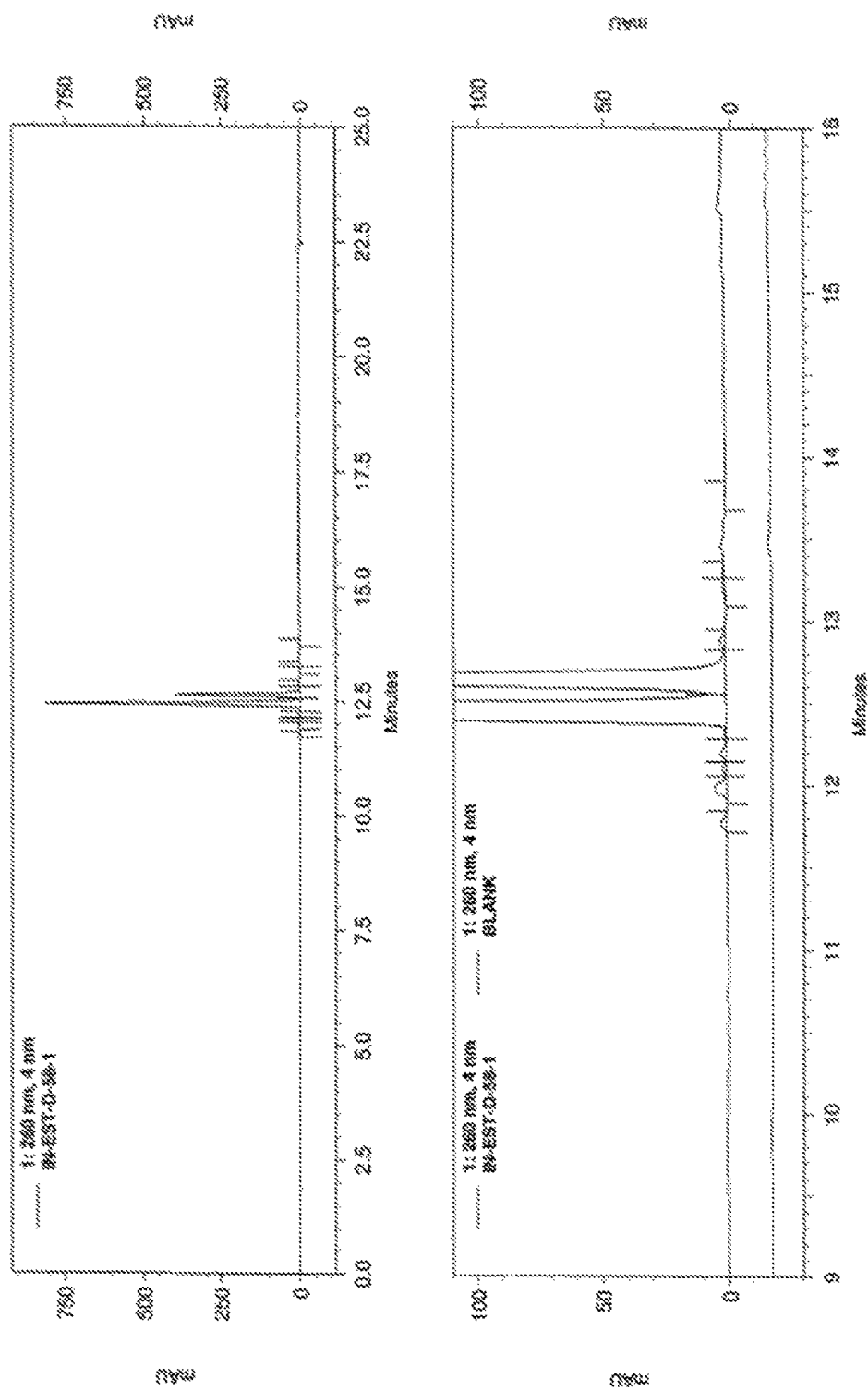

| Compound | Sodium Channel Site 2, 3H-Batrachotoxinin Binding ||||| Serotonin 5-HT₂A Receptor, 3H-Ketanserin Binding |||||
|---|---|---|---|---|---|---|---|---|---|---|
| | Maximal Concentration | Percentage Inhibition | IC$_{50}$ | Ki | nH | Maximal Concentration | Percentage Inhibition | IC$_{50}$ | Ki | nH |
| Example 1 | 1 µM | 65 | 0.39 µM | 0.35 µM | 0.68 | 10 µM | 88 | 1.22 µM | 0.35 µM | 0.95 |
| Example 1A | 1 µM | 53 | 0.78 µM | 0.71 µM | 0.89 | 30 µM | 85 | 6.59 µM | 1.88 µM | 1.16 |
| Example 1B | 10 µM | 84 | 1.91 µM | 1.75 µM | 0.84 | 30 µM | 87 | 5.90 µM | 1.69 µM | 1.11 |
| Example 1C | 1 µM | 68 | 0.39 µM | 0.35 µM | 0.86 | 1 µM | 60 | 0.61 µM | 0.17 µM | 0.80 |
| Example 1D | 1 µM | 61 | 0.43 µM | 0.39 µM | 0.66 | 10 µM | 75 | 3.03 µM | 0.86 µM | 0.86 |
| Example 1E | 1 µM | 66 | 0.51 µM | 0.46 µM | 0.89 | 3 µM | 66 | 1.46 µM | 1.46 µM | 0.89 |
| Dibucaine | nd | nd | 0.68 µM | 0.62 µM | 1.23 | nd | nd | nd | nd | nd |
| Ketanserin | nd | nd | nd | nd | nd | nd | nd | 0.47 nM | 0.14 nM | 1.06 |

FIGURE 5

USE OF TETRAHYDROPYRIDINES IN THE TREATMENT OF SODIUM CHANNEL RELATED DISEASE AND DISORDERS

CROSS-REFERENCE TO RELATED APPLICATIONS

This application is the National Phase under 35 U.S.C. § 371 of PCT International Application No. PCT/SG2015/050461, filed Nov. 19, 2015, which claims the benefit and priority of Singapore Application No. 10201408115S, filed Dec. 5, 2014, the entire contents of the aforementioned applications are hereby incorporated herein by reference.

FIELD OF INVENTION

The present invention relates generally to sodium channel related diseases and disorders, including but not limited to hyperactivity related, muscular, bladder, immune system and neurological disorders.

BACKGROUND OF INVENTION

The following discussion of the background of the invention is intended to facilitate an understanding of the present invention. However, it should be appreciated that the discussion is not an acknowledgement or admission that any of the material referred to was published, known or part of the common general knowledge in any jurisdiction as at the priority date of the application.

Sodium channels are the founding members of the superfamily of ion channels that includes voltage gated potassium and calcium channels. Unlike the different classes of potassium and calcium channels, however, functional properties of the known sodium channels (NaV) are relatively similar. Voltage gated sodium site 2 channels which are found in central neurons, are primarily localized to unmyelinated and pre-myelinated axons, govern action potential initiation and repetitive firing. Sodium channels play an important role in the neuronal network by transmitting electrical impulses rapidly throughout cells and cell networks, thereby coordinating higher processes including but not limited to locomotion, cognition and pain. These channels are large transmembrane proteins, which are able to switch between different states to enable selective permeability for sodium ions. For this process an action potential is needed to depolarize the membrane, and hence these channels are voltage-gated.

Voltage-gated sodium channels are classified based on their sensitivity to tetrodotoxin, from low nanomolar (Tetrodotoxin sensitive, TTXs) to high micromolar (Tetrodotoxin resistant, TTXr). So far, 9 different sodium channel α subunits have been identified and classified as $Na_V$ 1.1 to $Na_V$ 1.9. $Na_V$ 1.1 to $Na_V$ 1.4, $Na_V$ 1.6 and $Na_V$ 1.7 are TTXs, whereas $Na_V$ 1.5, $Na_V$ 1.8 and $Na_V$ 1.9 are TTXr, with different degrees of sensitivity. $Na_V$ 1.1 to $Na_V$ 1.3 and $Na_V$ 1.6 are primarily expressed in the central nervous system (CNS), whereas $Na_V$ 1.4 and $Na_V$ 1.5 are mainly expressed in muscle (skeletal and heart respectively). $Na_V$ 1.7, $Na_V$ 1.8 and $Na_V$ 1.9 are predominantly expressed in dorsal root ganglion (DRG) sensory neurons.

Several diseases, disorders and their symptoms, are related to abnormal sodium channel conductance. These include hyperactivity related, muscular, bladder, immune system, neurological disorders, pain, convulsion, inflammation and even cancer. Voltage-gated sodium channels expressed in non-nervous or non-muscular organs are often associated with the metastatic behaviour of different cancers and have been implicated in the pathology of different cancers such as prostate, breast, lung (small cells and non-small cells) and leukaemia (Roger S et al., Curr Pharm Des 2006, 12(28):3681-3695; Li M and Xiong Z G, Int J Physiol Pathophysiol Pharmacol 2011, 3(2):156-166).

Autism spectrum disorder (ASD) is characterized by social deficits and communication difficulties, stereotyped or repetitive behaviours and hyperactivity. Through whole exome sequencing, candidate genes with de novo mutations, including SCN1A which codes for $Na_V$ 1.1, have been recently identified in sporadic ASD (Eijkelkamp et al., Brain, 2012, 135, 2585-2612). Although initially thought to be different, it has been recently found that autism, attention deficit-hyperactivity disorder (ADHD), bipolar disorder, major depressive disorder and schizophrenia, all share common genetic underpinnings (Soretti A and Fabbri C, Lancet, 2013, 381 (9875), 1339-1341). These disorders, their pathophysiology and current treatment are summarized in the fifth revision of the American Psychiatric Association's Diagnostic and Statistical Manual of Mental Disorders $5^{th}$ edition (DSM-5), published in 2013, and the Encyclopedia of Psychopharmacology (Springer 2010).

Voltage-gated sodium channel channelopathies such as paramyotonia congenital and periodic paralysis affecting skeletal muscles can be found in SCN4A/$Na_V$1.4. Mutations in $Na_V$ 1.4 can result in ionic leak through the gating pore allowing sustained inward sodium flux at negative membrane potentials. Such mutations can also enhance activation or impair inactivation resulting in hyperexcitability (Eijkelkamp et al., Brain, 2012, 135, 2585-2612).

It is believed that changes in the isoforms of sodium channels cause abnormal ectopic firing of the DRG, causing spontaneous ectopic discharges. This can lead to an overactive bladder, characterized by urgency, frequency and nocturia, with or without urge incontinence (Steers W D, Rev Urol 2002, 4 (Suppl4), S7-S18).

In multiple sclerosis, demyelination of axons occur in patients, which lead to ectopic action potential firing that is caused by slow sodium-dependent membrane potential oscillations (Eijkelkamp et al., Brain, 2012, 135, 2585-2612).

Mutations in the gene encoding $Na_V$ 1.1 and $Na_V$ 1.2 have shown to be involved in the pathophysiology of both acquired and inherited epilepsy, where the active state of sodium channels are favoured, resulting in the potentiation of electrical signal propagation which leads to maximal seizure activity and its spread (Zuliani V. et al., Curr Top Med Chem, 2012, 12(9), 962-70).

A number of drugs having an unknown mechanism of action actually act by modulating sodium channel conductance, including local anesthetics, class I antiarrhythmics and anticonvulsants. Ion channel targeted drugs have always been related with either the CNS, the peripheral nervous system, or the cardiovascular system (Waszkielewicz A M et al., Curr Med Chem, 2013, 20, 1241-1285). Neuronal sodium channel blockers have found application with their use in the treatment and alleviation of the abovementioned diseases, disorders and symptoms, for example, epilepsy (phenyloin and carbamazepine), bipolar disorder (lamotrigine), preventing neurodegeneration, and in reducing neuropathic pain. Various antiepileptic drugs that stabilize neuronal excitability are effective in neuropathic pain (e.g. carbamazepine).

However, there is still a need for improved methods and compounds in treating and alleviating sodium channel related diseases, disorders and symptoms, for example lowering dosage but maximising drug effects in addressing these diseases, disorders and symptoms.

Threo- and erythro-diastereomers of methylphenidate are known to bind to dopamine and serotonin receptors, where the threo form is commonly prescribed to patients as a racemate for the treatment of ADHD (Davies H. M. L. et al., Bioorg Med Chem Lett, 2004, 14, 1799-1802). This is iterated in WO 2007106508 A2 where methylphenidate also interacts with norepinephrine, serotonin and dopamine transporters, most of them in the micromolar range. However, the present inventors have found that methylphenidate and its analogues, strongly bind to sodium channels, in particular to sodium channel site 2—this is not disclosed nor suggested in the prior art. Further, the $IC_{50}$ values for the antagonistic binding activity of the compound in WO 2007106508 A2 to serotonin 5-HT2A and 5-HT2C receptors are in the micromolar range, which should not be sufficient to elucidate the desired pharmacological effects. Moreover, the synthesis of the methylphenidate analogues in WO 2007106508 A2 involve a rhodium catalyst which will be an issue in an active pharmaceutical product since the amount of heavy metals is strictly regulated and is limited to rhodium at 10 ppm for oral dosing and 1 ppm for parental administration.

Therefore the object of the present invention is to provide for an improved use of methylphenidate analogues for the treatment of sodium channel related diseases and disorders. The present invention also provides an improved process of synthesizing methylphenidate analogues to increase the safety and efficacy of the resultant compounds.

SUMMARY OF INVENTION

The present invention provides a method of treating one or more sodium channel related diseases or disorders in an individual, including related symptoms. The method comprises administering to the individual a tetrahydropyridine derivative in an amount effective to treat sodium channel related diseases or disorders in individuals. These compounds are generally categorised as Ritalin related compounds.

The present invention also provides compounds for use in the treatment of and also for use in the manufacture of a medicament for the treatment of sodium channel related diseases or disorders in an individual.

A method is further provided for the preparation and isolation of the derivatives of the compound of the present invention. Preferably, the threo- and erythro-diastereomers, and threo- and erythro-enantiomers are purified and isolated.

Sodium channel related diseases or disorders include but are not limited to hyperactivity related disorders (e.g. attention deficit hyperactivity disorder (ADHD), autism spectrum disorder (ASD) and schizophrenia-related hyperactivity), muscular disorders (e.g. bronchospasm and oesophageal spasm), bladder disorders (e.g. urinary incontinence and irritable bowel syndrome (IBS)), immune system disorders (e.g. multiple sclerosis), neurological disorders (e.g. schizophrenia, epilepsy and migraine) and cancer. Symptoms related to at least one of the above diseases or disorders include but are not limited to pain, convulsion and inflammation.

In particular embodiments, the compositions administered according to the method of the invention comprises a compound having the following general structure (1):

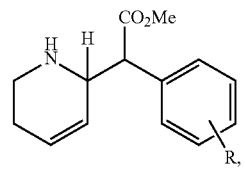

its diastereomer, enantiomer, racemic mixture, salts or a combination thereof, wherein R is selected from a group comprising hydrogen, alkyl, alkenyl, alkoxy, halo, nitro, cyano, keto, amino, carboxylate, substituted or unsubstituted phenyls, adjacent rings which share a side with the R-bearing group, or a combination thereof. The R-bearing group is preferably mono-, di-, or tri-substituted.

Preferably, the compound is a threo-diasteromer, erythro-diastereomer or a mixture of the threo-diastereomer and the erythro-diastereomer. It is preferable that the compound has one of the following structures (2 and/or 3):

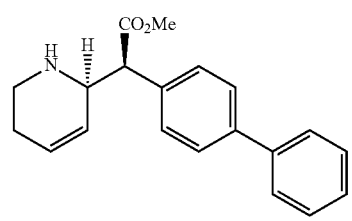

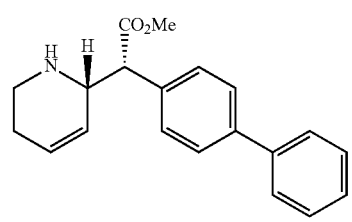

Preferably, the compound operates by inhibiting sodium channel conductance, where the sodium channels are voltage gated sodium channels. It is also preferred that the compound operates by binding to site 2 of voltage gated sodium channels.

Further, it is preferred that the compound also binds to serotonin receptors, particularly but not limited to serotonin $5\text{-HT}_{2A}$ receptors.

BRIEF DESCRIPTION OF FIGURES/DRAWINGS

The present invention will now be described, by way of example only, with reference to the accompanying drawing, in which:

FIG. 1 provides a HPLC trace of EXAMPLE 1 on an ECLIPSE XDB-C18, 5 μm, 4.6×150 mm column, flow 1 ml/min. Solvent phase A: 0.05% TFA in water, solvent phase B: 0.05% TFA in acetonitrile. Gradient (time/% B): 0/5 5/5 15/90 20/90 20.1/5 25/5.

Figure 2:
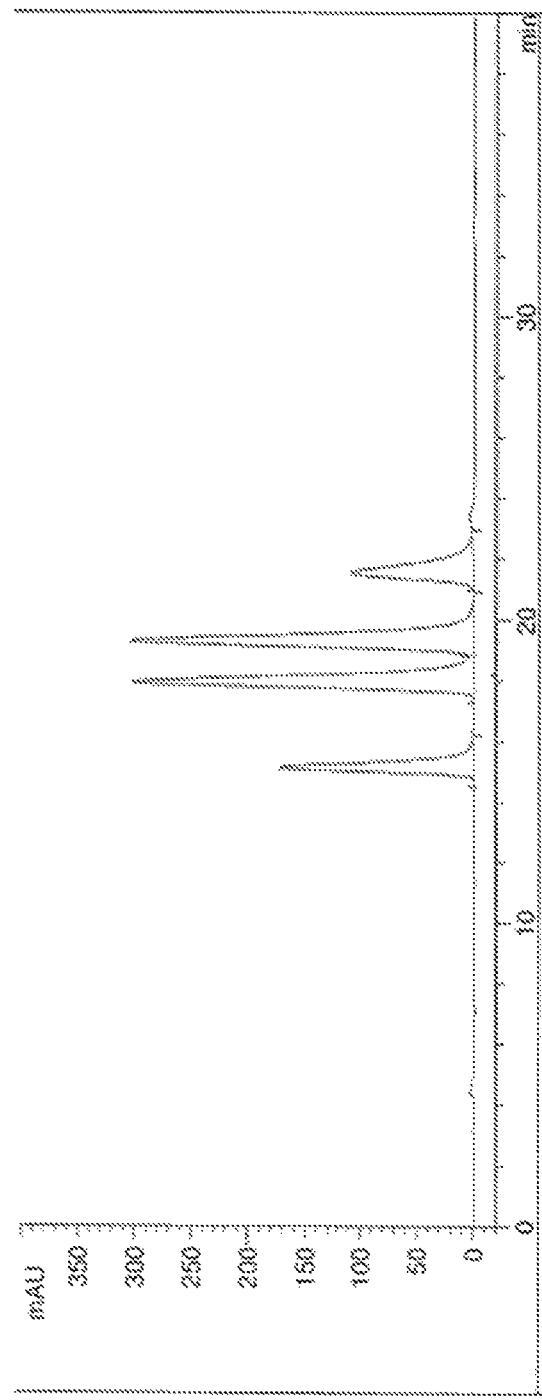

FIG. 2 provides a HPLC trace of EXAMPLE 1 on a Diacel chiralpak IA3, 3μ, 4.6×250 mm column, flow 1 ml/min. Solvent: 0.1% DEA in hexane:IPA (99:1%), isocratic.

Figure 3:
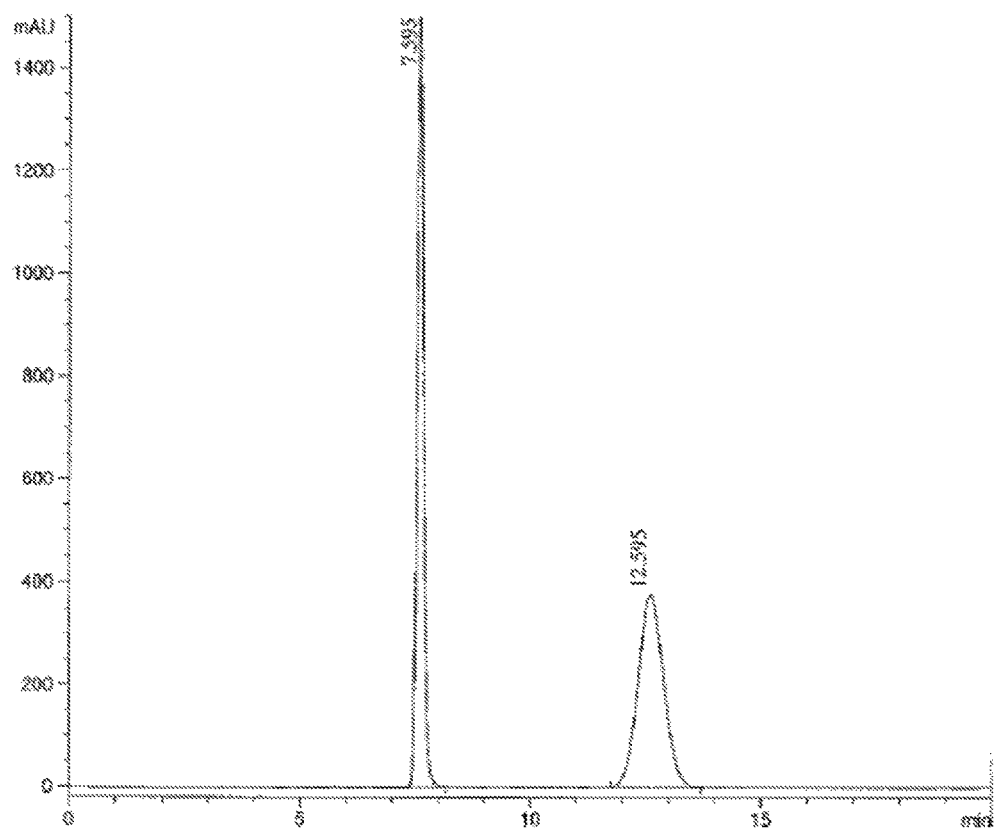

FIG. 3 provides an analytical HPLC trace of Enantiomer M and Enantiomer N separation on a Diacel CHIRALPAK IA3, 3μ, 4.6×250 mm column, flow 1 ml/min. Solvent: 0.1% DEA in hexane:Ethanol (99:1%), isocratic.

Figure 4:
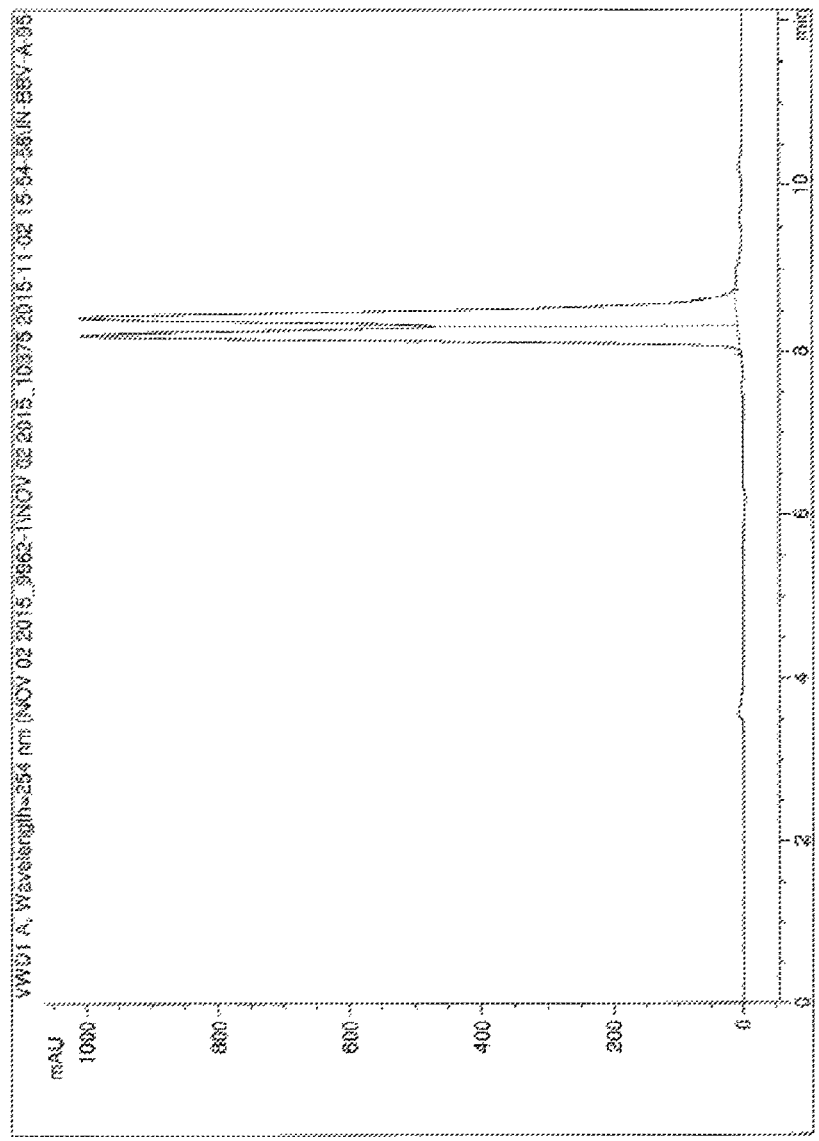

FIG. 4 provides an analytical HPLC trace of EXAMPLE 1E separation on a Diacel CHIRALPAK IA3, 3μ, 4.6×250 mm column, flow 1 ml/min. Solvent: 0.1% DEA in hexane: Ethanol (99:1%), isocratic. Both enantiomers are present in equal amounts.

FIG. 5 provides a table showing the results of the binding of the disclosed EXAMPLEs to sodium channel site 2 and serotonin 5-HT$_{2A}$ binding sites expressed in % binding at the maximal concentration tested as well as IC50, Ki and nH for concentration-response curves.

Figure 6:
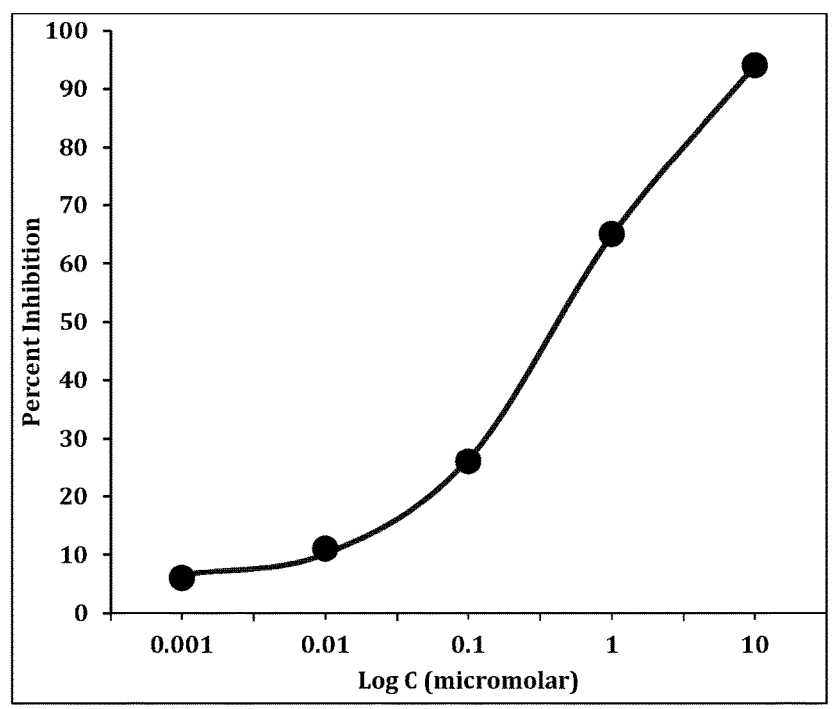

FIG. 6 provides a graph showing the percentage inhibition of [3H] Batrachotoxinin against log concentration (μm) of EXAMPLE 1.

DETAILED DESCRIPTION OF THE INVENTION

The present invention provides a method of treating one or more sodium channel related diseases or disorders in an individual, including related symptoms. The method comprises administering to the individual a tetrahydropyridine derivative in an amount effective to treat sodium channel related diseases or disorders in individuals.

The term "individual" used in the specification herein describes an animal, preferably a human.

It is contemplated that a constellation of sodium channel related diseases, disorders and symptoms in the same individual, can be treated or alleviated by the present invention. In this regard, recognising sodium channel related diseases, disorders and symptoms and the treatment and/or alleviation of the same, during or after practice of the present invention is well within the purview of a person having ordinary skill in the art and can be performed using any suitable clinical, diagnostic, observational or other techniques. Treatment of a disease or disorder is understood to include anything done or provided for alleviating or preventing the effects or symptoms of the disease or disorder, whether it is done or provided by way of cure or not. A reduction in any particular symptoms—including symptoms that are not a result of sodium channel related diseases or disorders, but are generally related to abnormal sodium channel conductance—resulting from practising the present invention, is considered an alleviation of the symptom.

Sodium channel related diseases or disorders generally involve abnormal sodium channels conductance and overexpressed sodium channels. Abnormal conductance across sodium channels can result from abnormal channel aperture and/or frequency of the opening/closing of the sodium channel due to mutations in sodium channel proteins or binding of small molecules to sodium channel protein sites. Such abnormal conductance include but are not limited to persistent sodium currents resulting from sodium channels generating much longer openings as a result of incomplete or defective fact inactivation and resurgent sodium currents which may arise following relief of ultra-fast open-channel block. It is also contemplated that overexpression of sodium channels may increase excitability of the cells (e.g. neurons) in which they are located. Accordingly, sodium channel related diseases or disorders include but are not limited to hyperactivity related disorders (e.g. attention deficit hyperactivity disorder (ADHD) and autism spectrum disorder (ASD)), muscular disorders (e.g. bronchospasm and oesophageal spasm), bladder disorders (e.g. urinary incontinence and irritable bowel syndrome (IBS)), immune system disorders (e.g. multiple sclerosis), neurological disorders (e.g. schizophrenia, epilepsy and migraine) and cancer. Symptoms related to at least one of the above diseases or disorders are well-known and include but are not limited to pain, convulsion and inflammation. Recognising and determining a reduction in the symptoms of any of these diseases or disorders can be readily performed by those skilled in the art.

Sodium channels described herein include but are not limited to sodium channels which channel openings are triggered by voltage change (e.g. voltage gated, voltage sensitive and voltage dependent sodium channels) or ligand binding (e.g. ligand gated sodium channels).

The compounds of the present invention can be understood to modulate sodium channel conductance by binding to sodium channels, for the purposes of treating sodium channel related diseases or disorders, where such modulation includes but is not limited to complete or partial inhibition, or reduction in sodium channel conductance.

Compositions comprising an effective amount of the compound may be administered via any conventional route. Such routes include but are not limited to orally, parenterally, intramuscularly, intravenously, mucosally and transdermally.

Determining a dosage regime of the compounds is well within the purview of those skilled in the art. By way of example, doses between 0.1 mg and 1,000 mg are considered. It will be recognised by that dosing parameters, in addition to the weight of the individual, also take into account the age of the individual and the stage of the disease or severity of the disorder, and can be determined according to conventional procedures.

Other components may be combined with the compounds to form pharmaceutical preparations for use in the present method. Such components can be selected depending on factors which include but are not limited to the dosage form, particular needs of the patient, and method of manufacture, among other things. Examples of such components include but are not limited to binders, lubricants, fillers, flavorings, preservatives, colorings, diluents, etc.

Additional information regarding pharmaceutical composition components for use with the present method are described in Remington's Pharmaceutical Sciences (18$^{th}$ Edition, A. R. Gennaro et al. Eds., Mack Publishing Co., Easton, Pa., 1990). Accordingly, the selection of particular substances and their compatibilities with the compositions of the present invention can be readily ascertained by those of ordinary skill in the art.

The compound and its diastereomers, enantiomers, racemic mixtures, salts (including but not limited to pharmaceutically acceptable salts, chiral salts and such chiral salts crystallized, e.g. lactic or tartaric acid), or any combination thereof, can function as sodium channel inhibitors, which have surprisingly shown to have significant therapeutic utility in humans. Said compound can also include any chiral stationary phase employed for the resolution of their enantiomers. For example, Lamotrigine, generally accepted to be a member of the sodium channel blocking class of antiepileptic drugs, has been shown to be a safe and effective treatment option for adult ADHD comorbid with bipolar and recurrent depression (Öncü et al., J Psychopharmacol, 2014, 28(3), 282-283). Furthermore, the compound and its derivatives of the present invention has been found to bind to serotonin receptors, in particular 5-HT$_{2A}$ receptors, acting as antagonists which are known as antipsychotic agents and which can improve cognitive function in patients. The compound and its derivatives have been found to inhibit and/or reduce the activity of serotonin receptors. This suggests that there is a combined activity of the compound and its derivatives on both sodium channel receptors and serotonin receptors, where such combination will be beneficial as the cognitive function will be improved and hyperactivity will be reduced. The dual functionality and mechanism can be applied specifically for the use in treatment-resistant settings.

The compounds in the present invention, including its diastereomers, enantiomers, racemic mixtures, diastereomeric mixtures and salts thereof, having the following general structure (1), have shown to exhibit favourable biological activity in in vitro pharmacological receptor studies:

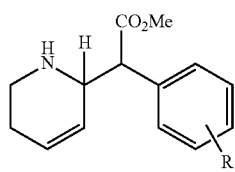

(1)

R is selected from a group comprising hydrogen, halo, substituted or unsubstituted phenyls, adjacent rings which share a side with the R-bearing group, or a combination thereof. It would be understood that R can also be selected from a group comprising alkyl, alkenyl, alkoxy, nitro, cyano, keto, amino and carboxylate. The R-bearing group is preferably mono-, di-, or tri-substituted. Preferably R represents one or more substituents selected from the group consisting of hydrogen, halogens, substituted or unsubstituted phenyls, and adjacent rings which share a side with the R-bearing group. Preferred are substituents such as hydrogen, unsubstituted phenyls, one or more chlorines, bromine, and single adjacent aromatic rings which, together with the R-bearing ring, comprise a naphthyl group. Accordingly, the term "derivative" refers to a compound or compounds which have the general structure (1) or are derived from compounds having the general structure (1) through a chemical or physical process, and includes but is not limited to diastereomers, enantiomers and salts.

R-groups in the para-position of the R-bearing ring, such as an unsubstituted phenyl in the para-position on the R-bearing ring; chlorine substituents at either or both the meta and/or para positions, a bromine substituent at the para-position; and one adjacent ring such that, together with the R-bearing ring, it comprises a para-2-naphthyl group, are preferred. It is preferably that the compound has the structure (2) and/or structure (3):

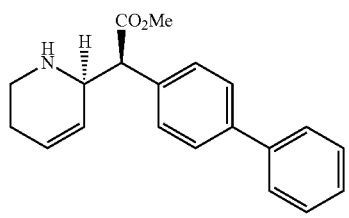

(2)

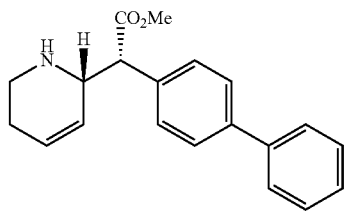

(3)

The synthesis of the compound having the general structure (1), its threo- and erythro-diastereomers and enantiomers are described herein. The synthesis reaction includes the use of a non-chiral rhodium catalyst (rhodium (II) octanoate dimer). The choice of the catalyst comes with a significant reduction in costs and allows the access of a new synthetic route which moves the use of the rhodium catalyst to an earlier step in the synthetic route. While a rhodium catalyst is used in said synthesis reaction, said reaction avoids rhodium catalyst in the last reaction steps, which is useful since the compounds described herein are intended generally for pharmaceutical applications, whereby the amount of heavy metals is heavily regulated and is limited for Rhodium at 10 ppm for oral dosing and 1 ppm for parenteral administration. Accordingly, the rhodium catalyst and any rhodium derivatives are substantially removed from the mixture containing the compound of the present invention, including its threo- and erythro-diastereomers and enantiomers, where the term "substantially" means that the amount of rhodium remaining in the mixture, is equal to or less than 10 ppm for oral dosing, or 1 ppm for parental administration. Suitable purification and isolation techniques to obtain the final chemical products (i.e. the threo- and erythro-diastereomers and enantiomers) of the reaction can be readily determined according to conventional procedures, for example by means of column chromatography, chiral high-performance liquid chromatography (HPLC) and crystallisation. For the avoidance of doubt, a protecting group used herein refers to a chemical group which is capable of reacting with a functional group in a compound, for the purposes of protecting the functional group from a reaction. Protecting groups include but are not limited to tert-Butyloxycarbonyl (BOC), carbobenzyloxy (Cbz), p-Methoxybenzyl carbonyl (Moz) and acetyl (Ac) groups.

While the invention is illustrated by way of the following examples, the examples are meant only to illustrate particular embodiments of the present invention and are not meant to be limiting in any way.

PREPARATION EXAMPLES

This representation provides representative procedures for making the compound having the structure (2), its threo- and erythro-diastereomers, and enantiomers. The steps of this example would be understood by a person having ordinary skill in the art to also apply to the synthesis of other tetrahydropyridine derivatives with the general formula (1), where the utilization of different reactants and implementation of different experimental conditions would be routine for a skilled person in order to optimise the synthesis of the desired compounds.

Preparation of EXAMPLE 1

The general synthesis of the compound having structure (2) is summarized and exemplified for EXAMPLE 1. Synthesis of EXAMPLE 1 was achieved in five steps, starting from the commercially available 2-[(1,1'-biphenyl)-4-yl] acetic acid Compound A. Compound A was esterified followed by treatment with tosyl azide to afford Intermediate C, which was treated with D in presence of Rh (II) octanoate to afford Intermediate E as an inseparable mixture of diastereomers. Intermediate E was subjected to Boc-removal with TFA to afford Intermediate F, which upon treated with HCl-MTBE to afford EXAMPLE 1 (Scheme 1).

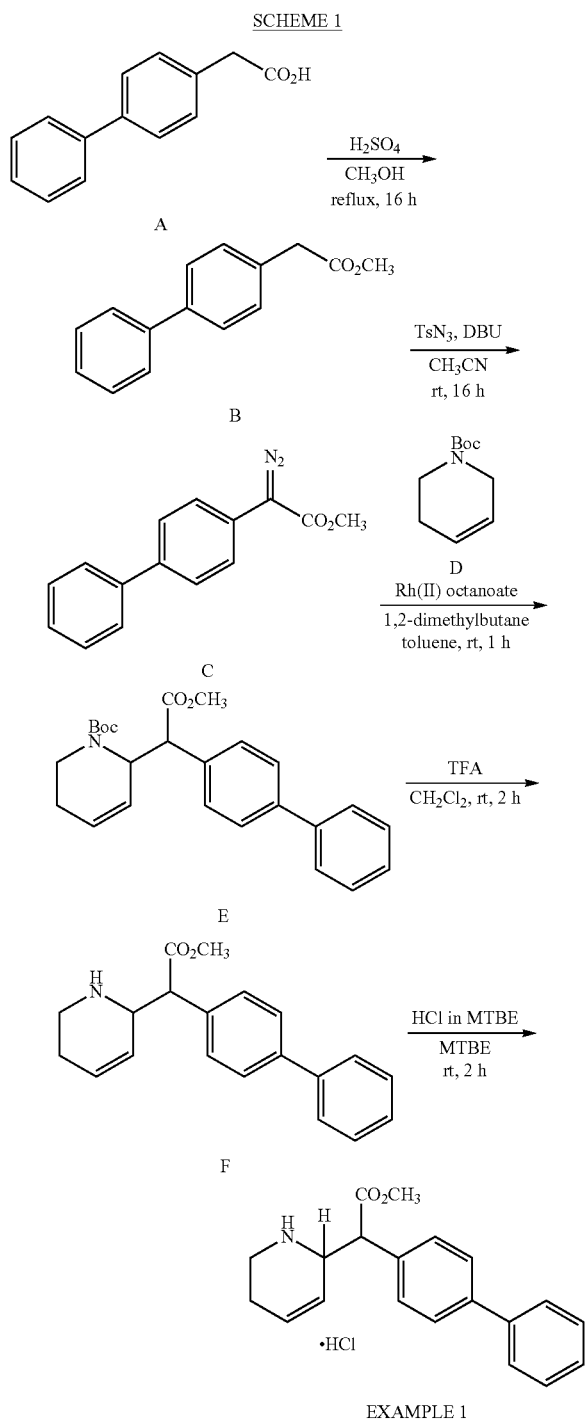

SCHEME 1

EXAMPLE 1

1. Preparation of methyl biphenyl-4-ylacetate, Intermediate B

A solution of biphenyl-4-ylacetic acid (10.0 g, 47.1 mmol) in MeOH (100 mL) was charged with sulfuric acid (10 mL) at 0° C. The reaction mixture was stirred to reflux for 16 h. The reaction mixture was concentrated under the reduced pressure, diluted with ice water (100 mL) and was extracted with MTBE (2×100 mL). The combined organic layers were washed with saturated NaHCO$_3$ solution (100 mL), water (100 mL) and brine (50 mL). The organic layers were dried over anhydrous Na$_2$SO$_4$ and were concentrated under reduced pressure to afford methyl biphenyl-4-ylacetate (Intermediate B, 9.80 g, 92%) as a colourless liquid.

$^1$H NMR (CDCl$_3$): δ 7.49-7.44 (m, 4H), 7.35-7.23 (m, 5H), 3.60 (s, 3H), 3.56 (s, 2H).

2. Preparation of Methyl [2-(biphenyl-4-yl)-diazoacetate, Intermediate C

A solution of methyl biphenyl-4-ylacetate (Intermediate B, 9.80 g, 43.3 mmol) in acetonitrile (50 mL) was charged with DBU (9.80 g, 65.0 mmol) followed by a solution of tosylazide (10.2 g, 52.0 mmol) in acetonitrile (48 mL) dropwise at 0° C. over 10 min. The reaction mixture was stirred at room temperature for 16 h. The reaction mixture was concentrated under reduced pressure, diluted with 5% KOH solution (200 mL) and was extracted with MTBE (3×200 mL). The combined organic layers were washed with water (100 mL) and brine (50 mL). The organic layers were dried over anhydrous Na$_2$SO$_4$ and were concentrated under reduced pressure to afford methyl [2-(biphenyl-4-yl)-diazoacetate (Intermediate C, 9.00 g, 82%) as a yellow solid.

$^1$H NMR (CDCl$_3$): δ 7.64-7.53 (m, 6H), 7.46-7.31 (m, 3H), 3.88 (s, 3H).

3. Preparation of tert-butyl 6-(2-methoxy-2-oxo-1-phenylethyl)-3,6-dihydropyridine-1(2H)-carboxylate, Intermediate E A solution of Rhodium (II) octanoate dimer (0.30 g, 0.39 mmol) in 1,2-dimethylbutane (200 mL) was charged with a solution of tertbutyl 5,6 dihydropyridine-1(2H)-carboxylate (Intermediate D, 11.1 g, 63.4 mmol) in 1,2-dimethylbutane (100 mL) at room temperature. [2-(biphenyl-4-yl)-diazoacetate (Intermediate C, 4.00 g, 15.8 mmol) in 1,2-dimethylbutane and toluene (300 mL, 2:1) were added to the reaction mixture dropwise over 15 min at room temperature. The reaction mixture was stirred at room temperature for 1 h. The reaction mixture was concentrated under reduced pressure and the residue was purified by column chromatography to afford tertbutyl 6-(2-methoxy-2-oxo-1-phenylethyl)-3,6-dihydropyridine-1(2H)-carboxylate (Intermediate E, 3.00 g, 46%) as an off-white solid.

$^1$H NMR (CDCl$_3$): δ 7.52-7.42 (m, 4H), 7.39-7.24 (m, 5H), 5.86-5.74 (m, 2H), 4.20-4.15 (m, 1H), 3.74 (d, J=10.4 Hz, 1H), 3.64 (s, 3H), 2.88-2.81 (m, 1H), 2.27-2.15 (m, 1H), 1.98-1.77 (m, 1H), 1.46-1.39 (m, 1H), 1.09 (s, 9H).

4. Preparation of methyl biphenyl-4-yl(1,2,5,6-tetrahydropyridin-2-yl)acetate, Intermediate F A solution of tert-butyl 6-(2-methoxy-2-oxo-1-phenylethyl)-3,6-dihydropyridine-1(2H)-carboxylate (Intermediate E, 3.00 g, 7.37 mmol) in CH$_2$Cl$_2$ (30 mL) was charged with TFA (5.7 mL, 74 mmol) dropwise at 0° C. over 5 min. The reaction mixture was stirred at room temperature for 2 h. The reaction mixture was concentrated under reduced pressure and was cooled to 0° C. The reaction mixture was basified to pH 10 with saturated NaHCO₃ solution (25 mL), extracted with CH₂Cl₂ (3×20 mL), washed with water (10 mL) and brine (10 mL). The combined organic extracts were dried over anhydrous Na2SO4 and were concentrated under the reduced pressure. The residue was purified by column chromatography to afford methyl biphenyl-4-yl(1,2,5,6-tetrahydropyridin-2-yl)acetate (Intermediate F, 2.00 g, 88%) as an off-white solid.

$^1$H NMR(CDCl₃): δ 7.59-7.55 (m, 4H), 7.49-7.32 (m, 5H), 5.91-5.69 (m, 2H), 5.30-5.27 (m, 1H), 4.04-3.99 (m, 1H), 3.70-3.69 (d, J=3.6 Hz, 3H), 3.65-3.57 (m, 1H), 3.09-2.76 (m, 2H), 2.22-2.05 (m, 1H), 2.04-1.98 (m, 1H).

5. Preparation of EXAMPLE 1, methyl biphenyl-4-yl(1,2,5,6-tetrahydropyridin-2-yl)acetate hydrochloride salt A solution of 6 (2.00 g, 6.5 mmol) in MTBE (20 mL) was charged with HCl in diethyl ether (1.0 M, 32 mL, 32 mmol) over 2 min at 0° C. The reaction mixture was stirred at room temperature for 2 h. The resulted solid was collected by filtration, washed with pentane (100 mL) and was dried under vacuum to afford EXAMPLE 1 (methyl biphenyl-4-yl(1,2,5,6-tetrahydropyridin-2-yl)acetate hydrochloride salt, 1.50 g, 67%, 98.7% AUC by HPLC) as an off-white solid. The two diastereomers in EXAMPLE 1 elute from an ECLIPSE XDB-018 column with retention times of 12.4 min and 12.6 min, respectively (FIG. 1), in a ratio of 2.16:1. On a chiral Diacel column, all 4 enantiomers can be analytically separated with retention times of 14.5 min, 18.0 min, 19.5 min and 21.5 min, respectively (FIG. 2).

$^1$H NMR (DMSO-d6): δ 9.73 (d, J=6.0 Hz, 1H), 9.39 (s, 0.3H), 8.62 (s, 0.7H), 7.75-7.39 (m, 9H), 6.07-5.90 (m, 1H), 5.69 (d, J=10.8 Hz, 0.7H), 5.19 (d, J=10.2 Hz, 0.3H), 4.49-4.52 (m, 1H), 4.15-4.30 (m, 1H), 3.67 (d, J=3.3 Hz, 3H), 3.50 (s, 1H), 3.22-3.03 (m, 2H), 2.22 (t, J=13.5 Hz, 1H).

Preparation of the EXAMPLE 1 Enantiomers: EXAMPLE 1A, EXAMPLE 1B, EXAMPLE 1C and EXAMPLE 1D Synthesis of EXAMPLE 1A, EXAMPLE 1B, EXAMPLE 1C and EXAMPLE 1D were followed up to the synthesis of the diastereomers of Intermediate F from the commercially available 2-[(1,1'-biphenyl)-4-yl]acetic acid the method as described above. Biphenyl-4-yl acetic acid was esterified followed by treatment with tosyl azide to afford Intermediate C, which was treated with Intermediate D in presence of Rh(II) octanoate to afford Intermediate E as an inseparable mixture of diastereomers. Intermediate E was subjected to Boc-removal followed by purification by silica chromatography to afford the Diastereomers of Intermediate F, erythro-Diastereomer G and threo-Diastereomer H (Scheme 2).

SCHEME 2

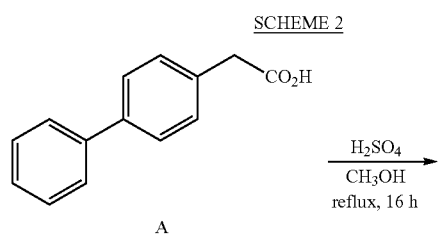

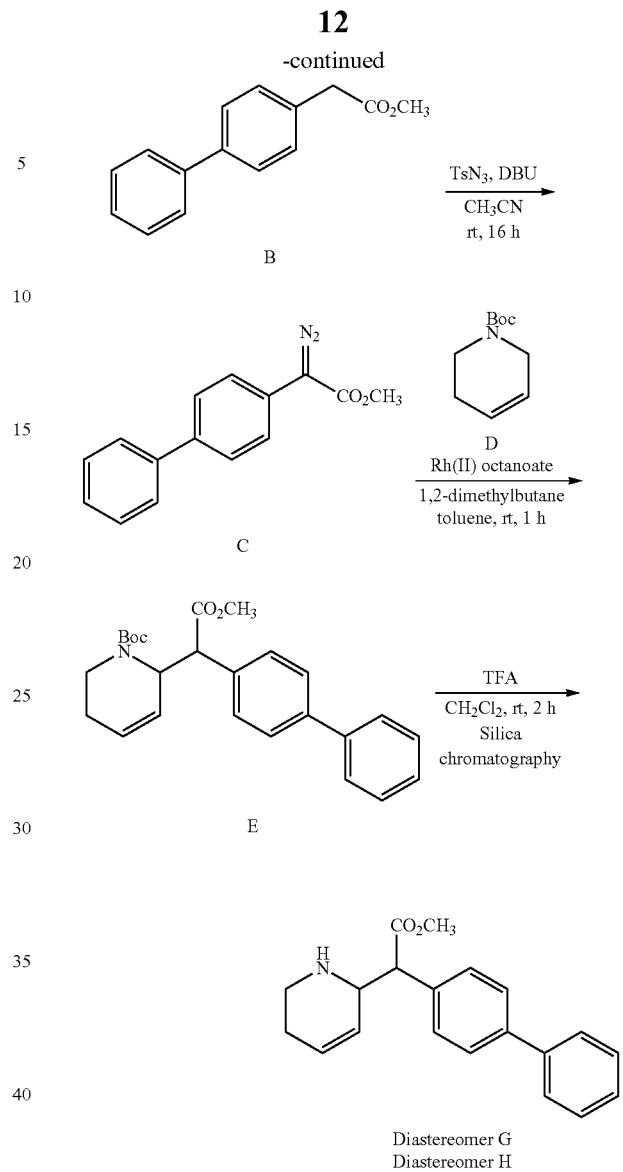

Diastereomer G was subjected to chiral-prep-HPLC to afford Enantiomers I and K, which upon treated with HCl to afford EXAMPLE 1A and EXAMPLE 1B (Scheme 3). Absolute stereochemistry of EXAMPLE 1A and EXAMPLE 1B were not assigned.

SCHEME 3

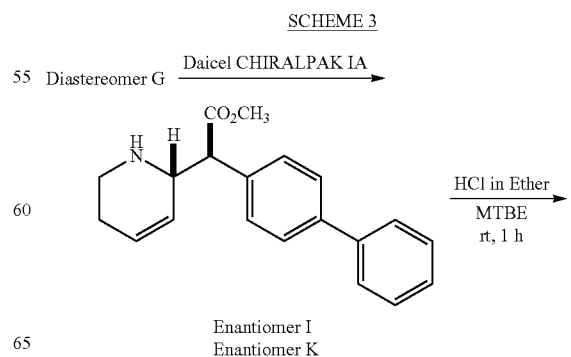

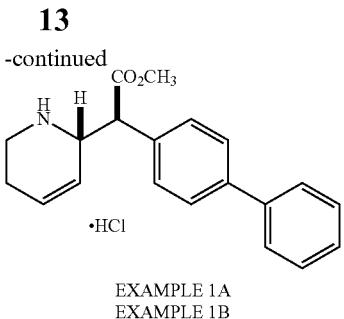

EXAMPLE 1A
EXAMPLE 1B

Diastereomer H was treated with Boc-anhydride to afford Intermediate L, which was subjected to chiral-prep-HPLC purification to afford Enantiomers M and N. Enantiomers M and N on removal of Boc with TFA afforded Enantiomers O and P, which were treated with HCl to afford EXAMPLE 1C and EXAMPLE 1D, respectively (Scheme 4).

SCHEME 4

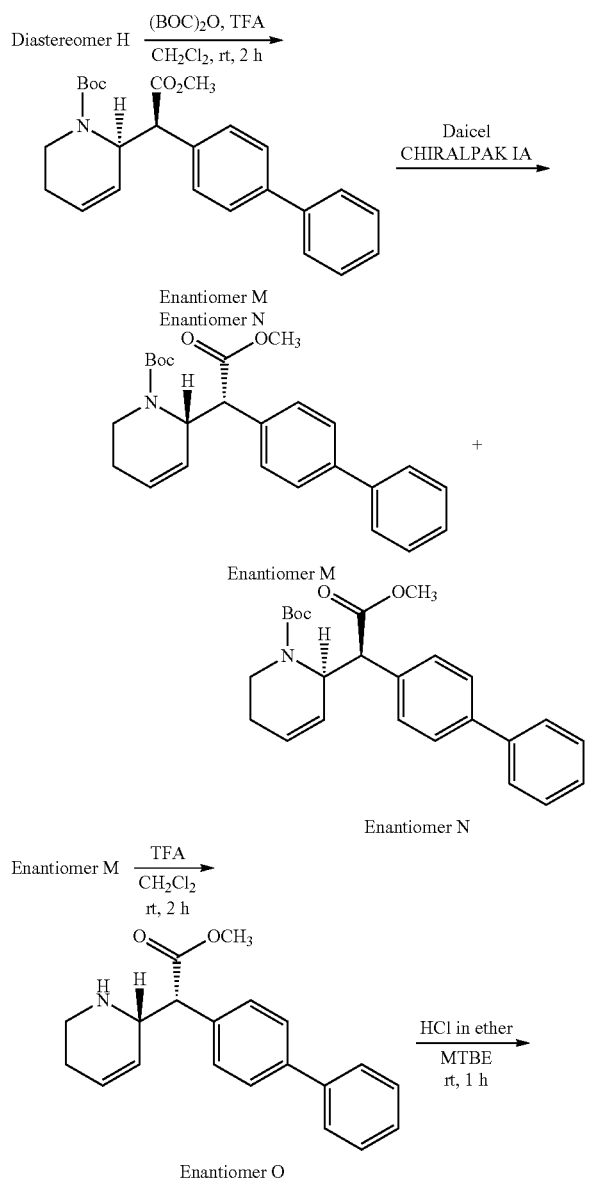

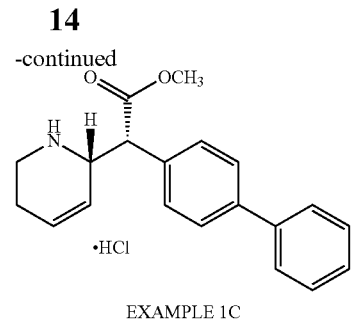

EXAMPLE 1C

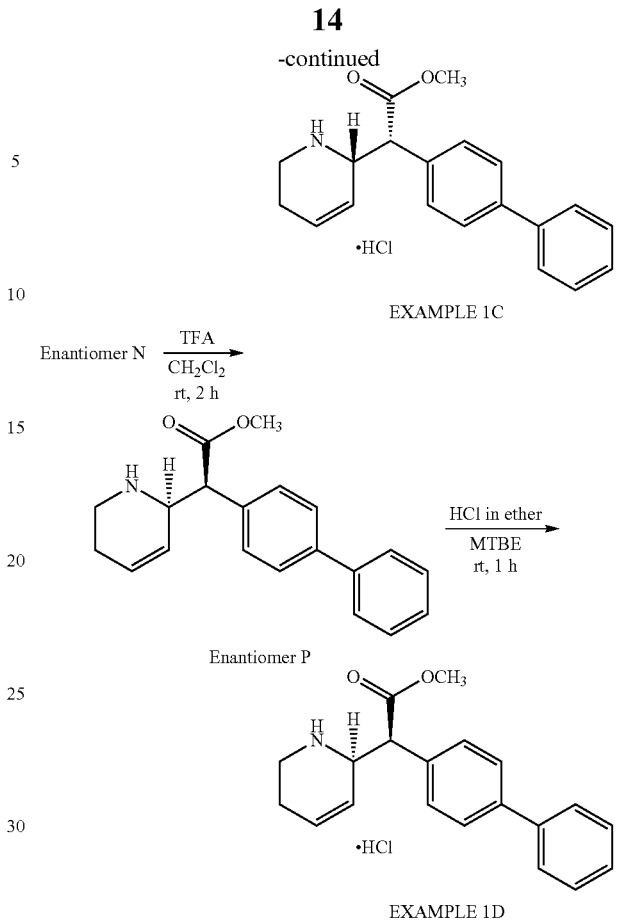

EXAMPLE 1D

1. Preparation of Erythro-Enantiomers I, K and Threo-Diastereomer H

A solution of Intermediate E (2.80 g, 6.80 mmol) in $CH_2Cl_2$ (28 mL) was charged with TFA (5.29 mL, 68.0 mmol) dropwise at 0° C. over 5 min. The reaction mixture was stirred at room temperature for 2 h. The reaction mixture was concentrated under reduced pressure and was cooled to 0° C. The reaction mixture was basified to pH≈10 with saturated $NaHCO_3$ solution (25 mL), extracted with $CH_2Cl_2$ (3×20 mL), washed with water (10 mL) and brine (10 mL). The reaction mixture was dried over anhydrous $Na_2SO_4$ and was concentrated under reduced pressure. The residue was purified by column chromatography to afford Erythro-Diastomer G (0.60 g) and Threo-Diastereomer H (0.90 g, 42%) as off-white solids. Erythro-Diastereomer G (0.60 g) was purified by chiral prep HPLC (0.1% of DEA in hexane:IPA, 99:1, Daicel CHIRALPAK IA, 250 mm×20 mm, 5µ, 12 mL/min; 0.60 g of mixture was dissolved in 30 mL of mobile phase and 4.0 mL was injected every 30 min) to afford Enantiomer I (0.20 g, 9.5%) as a first eluting enantiomer (22 min) followed by Enantiomer K (0.20 g, 9.5%) as a second eluting enantiomer (26 min) as off-white solids.

Enantiomers I and K:

$^1$H NMR (400 MHz, $CDCl_3$): δ 7.51-7.47 (m, 4H), 7.37-7.31 (m, 4H), 7.28-7.24 (m, 1H), 5.73-5.68 (m, 1H), 5.23-5.20 (m, 1H), 3.97-3.39 (m, 1H), 3.61 (s, 3H), 3.51 (d, J=10.4 Hz, 1H), 3.04-2.99 (m, 1H), 2.88-2.82 (m, 1H), 2.15-2.05 (m, 1H), 1.92-1.85 (m, 2H).

Threo-Diastereomer H:
¹H NMR (400 MHz, CDCl₃): δ 7.58-7.56 (m, 4H), 7.48-7.41 (m, 4H), 7.36-7.32 (m, 1H), 5.91-5.87 (m, 1H), 5.73-5.69 (m, 1H), 4.02-3.98 (m, 1H), 3.69 (s, 3H), 3.62 (d, J=10.4 Hz, 1H), 3.00-2.95 (m, 1H), 2.82-2.76 (m, 1H), 2.21-2.12 (m, 1H), 2.04-2.02 (m, 1H).

2. Preparation of Biphenyl-4-yl[-1,2,5,6-tetrahydropyridin-2-yl]acetate hydrochloride, EXAMPLE 1A A solution of Enantiomer I (0.18 g, 0.58 mmol) in MTBE (13.5 mL) was charged with HCl in diethyl ether (1.0 M, 2.93 mL, 2.93 mmol) over 2 min at room temperature. The reaction mixture was stirred at room temperature for 1 h. The reaction mixture was concentrated under the reduced pressure. The residue was triturated with pentane (20 mL), filtered and was dried under vacuum to afford (S,S)-biphenyl-4-yl[-1,2,5,6-tetrahydropyridin-2-yl]acetate hydrochloride (EXAMPLE 1A, 0.17 g, 85%, >99% AUC by HPLC, >99.0% (ee), m/z 308 [M+H]+) as a light yellow solid.
¹H NMR (400 MHz, DMSO-d6): δ 9.63 (bs, 1H), 9.27 (bs, 1H), 7.72-7.67 (m, 4H), 7.49-7.36 (m, 5H), 5.92 (d, J=10.0 Hz, 1H), 5.19 (d, J=10.0 Hz, 1H), 4.57 (bs, 1H), 4.22 (d, J=9.6 Hz, 1H), 3.68 (s, 3H), 3.35-3.17 (m, 2H), 2.27 (bs, 2H); mp=187° C.-189° C.; [α]25 D −173.2° (c 0.05, CHCl₃).

3. Preparation of Biphenyl-4-yl[-1,2,5,6-tetrahydropyridin-2-yl]acetate hydrochloride, EXAMPLE 1B Using a similar procedure to that described for the preparation of EXAMPLE 1A, compound Enantiomer K (0.20 g, 0.65 mmol) afforded (R,R)-biphenyl-4-yl[-1,2,5,6-tetrahydropyridin-2-yl]acetate hydrochloride (EXAMPLE 1B, 0.19 g, 85%, 97.6% AUC by HPLC, 98.6% (ee), m/z 308 [M+H]+) as a light yellow solid.
¹H NMR (400 MHz, DMSO-d6): δ 9.63 (bs, 1H), 9.27 (bs, 1H), 7.72-7.67 (m, 4H), 7.49-7.36 (m, 5H), 5.92 (d, J=10.0 Hz, 1H), 5.19 (d, J=10.0 Hz, 1H), 4.57 (bs, 1H), 4.22 (d, J=9.6 Hz, 1H), 3.68 (s, 3H), 3.35-3.17 (m, 2H), 2.27 (bs, 2H); mp=187° C.-189° C.; [α]25 D +184.8° (c 0.05, CHCl₃).

4. Preparation of Enantiomers M and N

A solution of Diastereomer H (0.90 g, 6.80 mmol) in CH₂Cl₂ (40 mL) was charged with TEA (0.79 mL, 5.82 mmol) followed by a solution of (Boc)₂O (0.73 mL, 3.22 mmol) in CH₂Cl₂ (10 mL) dropwise over 5 min at 0° C. The reaction mixture was stirred at room temperature for 2 h. When TLC analysis showed consumption of starting material, the reaction mixture was diluted with water (50 mL) and was extracted with CH₂Cl₂ (2×30 mL). The combined organic layers were washed with brine (20 mL). The layers were dried over anhydrous Na₂SO₄ and were concentrated under the reduced pressure. The residue was purified by column chromatography to afford a mixture of enantiomers M and N (0.90 g), which was purified by chiral prep HPLC (0.1% of DEA in hexane:EtOH, 99:1%, Daicel CHIRALPAK IA, 250 mm×20 mm, 5µ, 10 mL/min, 1.0 mL loop, 0.90 g of enantiomeric mixture (FIG. 3) was dissolved in 80 mL of mobile phase and for every 10 min aliquots were injected) to afford Enantiomer N (0.20 g, 16.8%) as first eluting enantiomer (6 min) followed by Enantiomer M (0.20 g, 16.8%) as second eluting enantiomer (7 min) as off-white solids.

Enantiomers M and N:
¹H NMR (300 MHz, CDCl₃): δ 7.52-7.42 (m, 4H), 7.36-7.25 (m, 5H), 5.84-5.73 (m, 2H), 4.20-4.14 (m, 1H), 3.73 (d, J=10.2 Hz, 1H), 3.64 (s, 3H), 2.89-2.80 (m, 1H), 2.25-2.13 (m, 1H), 1.93-1.88 (m, 1H), 1.46-1.42 (m, 1H), 1.09 (s, 9H).

5. Preparation of Enantiomer O

A solution of Enantiomer M (0.20 g, 0.49 mmol) in CH2Cl2 (2.0 mL) was charged with TFA (0.37 mL, 4.9 mmol) dropwise at 0° C. over 1 min. The reaction mixture was stirred at room temperature for 2 h. The reaction mixture was concentrated under reduced pressure and was cooled to 0° C. The reaction mixture was basified to pH 10 with saturated NaHCO3 solution (5.0 mL), extracted with CH₂Cl₂ (3×5.0 mL), washed with water (5.0 mL) and brine (5.0 mL). The reaction mixture was dried over anhydrous Na₂SO₄ and was concentrated under reduced pressure. The residue was purified by column chromatography to afford Enantiomer O (0.10 g, 66%) as an off-white solid.
¹H NMR (400 MHz, CDCl₃): δ 7.58-7.56 (m, 4H), 7.48-7.41 (m, 4H), 7.36-7.32 (m, 1H), 5.91-5.86 (m, 1H), 5.73-5.70 (m, 1H), 4.02-3.98 (m, 1H), 3.69 (s, 3H), 3.62 (d, J=10.4 Hz, 1H), 3.01-2.95 (m, 1H), 2.82-2.76 (m, 1H), 2.21-2.12 (m, 1H), 2.04-1.98 (m, 1H).

6. Preparation of Methyl(2R)-biphenyl-4-yl[(2S)-1,2,5,6-tetrahydropyridin-2-yl]acetate hydrochloride, EXAMPLE 1C Using a similar procedure to that described for the preparation of EXAMPLE 1A, Enantiomer O (0.10 g, 0.32 mmol) afforded Methyl (2R)-biphenyl-4-yl[(2S)-1,2,5,6-tetrahydropyridin-2-yl]acetate hydrochloride, EXAMPLE 1C (0.11 g, 99%, 96.5% AUC by HPLC, 94.4% (ee), m/z 308 [M+H]+) as a light yellow solid.
¹H NMR (400 MHz, DMSO-d6): δ 9.55 (bs, 1H), 8.59 (bs, 1H), 7.74-7.68 (m, 4H), 7.58-7.37 (m, 5H), 6.05 (d, J=8.0 Hz, 1H), 5.69 (d, J=9.6 Hz, 1H), 4.50 (bs, 1H), 4.15 (d, J=10.4 Hz, 1H), 3.67 (s, 3H), 3.20-3.03 (m, 2H), 2.50 (bs, 1H), 2.22-2.18 (m, 1H); mp=194° C.-196° C.; [α]25 D +106.4° (c 0.05, CHCl₃).

7. Preparation of Enantiomer P

Using a similar procedure to that described for the preparation of Enantiomer O, compound Enantiomer N (0.20 g, 0.49 mmol) afforded Enantiomer P (0.10 g, 66%) as a light yellow solid.
¹H NMR (400 MHz, CDCl₃): δ 7.58-7.56 (m, 4H), 7.48-7.41 (m, 4H), 7.36-7.32 (m, 1H), 5.91-5.86 (m, 1H), 5.73-5.70 (m, 1H), 4.02-3.98 (m, 1H), 3.69 (s, 3H), 3.62 (d, J=10.4 Hz, 1H), 3.01-2.95 (m, 1H), 2.82-2.76 (m, 1H), 2.21-2.12 (m, 1H), 2.04-1.98 (m, 1H).

8. Preparation of Methyl(2S)-biphenyl-4-yl[(2R)-1,2,5,6-tetrahydropyridin-2-yl]acetate hydrochloride, EXAMPLE 1D Using a similar procedure to that described for the preparation of EXAMPLE 1C, Enantiomer P (0.10 g, 0.32 mmol) afforded Methyl (2S)-biphenyl-4-yl[(2R)-1,2,5,6-tetrahydropyridin-2-yl]acetate hydrochloride, EXAMPLE 1D (0.11 g, 99%, 96.1% AUC by HPLC, 98.2% (ee), m/z 308 [M+H]+) as a light yellow solid.
¹H NMR (400 MHz, DMSO-d6): δ 9.55 (bs, 1H), 8.59 (bs, 1H), 7.74-7.68 (m, 4H), 7.58-7.37 (m, 5H), 6.05 (d, J=8.0 Hz, 1H), 5.69 (d, J=9.6 Hz, 1H), 4.50 (bs, 1H), 4.15 (d, J=10.4 Hz, 1H), 3.67 (s, 3H), 3.20-3.03 (m, 2H), 2.50 (bs, 1H), 2.22-2.18 (m, 1H); mp=184° C.-186° C.; [α]25 D −98.0° (c0.05, CHCl$_3$).

Scalable procedure to obtain Methyl(2R)-biphenyl-4-yl[(2S)-1,2,5,6-tetrahydropyridin-2-yl]acetate hydrochloride, EXAMPLE 1C, and Methyl(2S)-biphenyl-4-yl[(2R)-1,2,5,6-tetrahydropyridin-2-yl]acetate hydrochloride, EXAMPLE 1D, as Enantiomeric Mixture In order to obtain a scalable procedure to obtain Methyl (2R)-biphenyl-4-yl[(2S)-1,2,5,6-tetrahydropyridin-2-yl]acetate hydrochloride, EXAMPLE 1C, and Methyl (2S)-biphenyl-4-yl[(2R)-1,2,5,6-tetrahydropyridin-2-yl]acetate hydrochloride, EXAMPLE 1D, as enantiomeric mixture starting from Intermediate C, the synthetic steps were optimized as follows:

1. Scalable Preparation of tert-butyl 6-(2-methoxy-2-oxo-1-phenylethyl)-3,6-dihydropyridine-1(2H)-carboxylate, Intermediate E A solution of Rhodium (II) octanoate dimer (1.00 g, 1.38 mmol) in n-hexane (50 mL) was charged to a solution of tertbutyl 5,6 dihdropyridine-1(2H)-carboxylate (Intermediate D, 10.1 g, 55.4 mmol) in n-hexane (100 mL) at room temperature. A solution of 3 (14.0 g, 55.4 mmol) in toluene (40 mL) was added to the above reaction mixture dropwise over 15 min. The reaction mixture was stirred at room temperature for 1 h. The reaction mixture was filtered through celite bed, washed with n-hexane (100 mL) and the filtrate was concentrated under reduced pressure to afford tert-butyl 6-(2-methoxy-2-oxo-1-phenylethyl)-3,6-dihydropyridine-1(2H)-carboxylate, Intermediate E, (24.0 g, crude) as a blue oil.

Analytical HPLC analysis of the crude product by Eclipse XDB-C18 column indicated the presence of the two diastereomers in 49% and 20%, respectively.

2. Scalable Preparation of methyl biphenyl-4-yl(1,2,5,6-tetrahydropyridin-2-yl)acetate, Intermediate F A solution 6-(2-methoxy-2-oxo-1-phenylethyl)-3,6-dihydropyridine-1(2H)-carboxylate (24.0 g, crude) in CH$_2$Cl$_2$ (150 mL) was charged with TFA (48 mL, 2 vol) dropwise at 0° C. over 15 min. The reaction mixture was stirred at room temperature for 2 h. The reaction mixture was concentrated under reduced pressure. The reaction mixture was diluted with CH$_2$Cl$_2$ (150 mL) and pH of the solution was adjusted to 10 with saturated NaHCO$_3$ solution (250 mL). The layers were separated and the aqueous layer was extracted with CH$_2$Cl$_2$ (3×200 mL). The combined organic layers were washed with water (200 mL) and brine (100 mL). The organic layers were dried over anhydrous Na$_2$SO$_4$ and concentrated under the reduced pressure to afford methyl biphenyl-4-yl(1,2,5,6-tetrahydropyridin-2-yl)acetate, Intermediate F (16.5 g, crude) as a brown oil.

Analytical HPLC analysis of the crude product by Eclipse XDB-C18 column indicated the presence of the two diastereomers in 41% and 22%, respectively.

3. Scalable Preparation of EXAMPLE 1, methyl biphenyl-4-yl(1,2,5,6-tetrahydropyridin-2-yl)acetate hydrochloride Salt A solution methyl biphenyl-4-yl(1,2,5,6-tetrahydropyridin-2-yl)acetate (16.5 g, crude) in 1,4-dioxane (100 mL) was charged with HCl in 1,4-dioxane (4 M, 33 mL, 2 vol) over 10 min at 0° C. The reaction mixture was stirred at room temperature for 2 h. The reaction mixture was concentrated under reduced pressure, washed with MTBE (50 mL) and was dried under vacuum to afford methyl biphenyl-4-yl(1,2,5,6-tetrahydropyridin-2-yl)acetate hydrochloride salt (EXAMPLE 1, 13.5 g, crude) as a light brown solid.

Analytical HPLC analysis of the crude product by Eclipse XDB-C18 column indicated the presence of the two diastereomers in 50% and 23%, respectively.

4. Scalable Preparation of EXAMPLE 1E (Enantiomeric Pair Consisting of Methyl(2R)-biphenyl-4-yl [(2S)-1,2,5,6-tetrahydropyridin-2-yl]acetate hydrochloride, EXAMPLE 1C, and Methyl(2S)-biphenyl-4-yl[(2R)-1,2,5,6-tetrahydropyridin-2-yl]acetate hydrochloride, EXAMPLE 1D)

A solution of methyl biphenyl-4-yl(1,2,5,6-tetrahydropyridin-2-yl)acetate hydrochloride salt (10.0 g, crude) in acetonitrile (40 mL) was charged with Methyl tert.-butyl ether (80 mL) and water (7.0 mL) at room temperature. The reaction mixture was stirred for 10 min at room temperature. The resulted solids were filtered, washed with Methyl tert.-butyl ether (25 mL) and was dried to afford EXAMPLE 1E (Enantiomeric pair consisting of Methyl (2R)-biphenyl-4-yl [(2S)-1,2,5,6-tetrahydropyridin-2-yl]acetate hydrochloride, EXAMPLE 1C, & Methyl (2S)-biphenyl-4-yl[(2R)-1,2,5,6-tetrahydropyridin-2-yl]acetate hydrochloride, EXAMPLE 1D, 3.75 g) as a light brown solid (96.8% HPLC purity, m/z 308 [M+H]+). The compound was found to be soluble in DMSO and acetonitrile/water. Chiral chromatography (FIG. 4) revealed the presence of both enantiomers in equal amounts.

WORKING EXAMPLES

This representation demonstrates the receptor binding properties of the compounds of the present invention. For this representation, the activities of EXAMPLE 1, EXAMPLE 1A, EXAMPLE 1B, EXAMPLE 1C, EXAMPLE 1D, and EXAMPLE 1E versus sodium channel site 2 and serotonin 5-HT2A binding sites were determined in radioligand binding studies. Functional studies on serotonin-induced IP1 increase in CHO cells were performed to determine agonist or antagonist activity.

Radioligand Binding Data

Sodium Channel Site 2 Binding:

The method employed in this study has been adapted from Catterall W A, Morrow C S, Daly J W and Brown C B (J Biol Chem. 256(17):8922-8927, 1981). Dibucain was used as reference standard as an integral part of each assay to ensure the validity of the results obtained:

Materials: [3H] Batrachotoxinin were prepared and purified as described. [3H] Batrachotoxinin is stable in storage for up to 1 year and is stable at 37° C. for the duration of these experiments.

Experimental: Whole brains (except cerebellum) of male Wistar derived rats weighing 175+/−25 g are used to prepare sodium channel site 2 in modified HEPES/Tris-HCl buffer: 130 mM choline chloride, 50 mM 4-(2-hydroxyethyl)-1-piperazineethanesulfonic acid (HEPES) 50 mM Tris adjusted to pH 7.4 at 37° C. 130 mM Choline Chloride, 5.4 mM KCl, 0.8 mM MgCl$_2$, 5.5 mM Glucose, 40 µg/ml scorpion venom from Leiurus quinquestriatus (LqTx). A 7.5 mg membrane aliquot is incubated with 5 nM [3H]Batrachotoxinin for 60 minutes at 37° C. Non-specific binding is estimated in the presence of 100 μM veratridine. Membranes are filtered and washed, the filters are then counted to determine [3H]Batrachotoxinin specifically bound. Compounds, dissolved in DMSO, are screened at a concentration range between 1 nM and 10 μM. In previous studies, the maximal binding capacity of [3H]Batrachotoxinin (Bmax) and its Kd were determined and amount to 0.70 pmol/mg Protein and 52 nM, respectively.

Serotonin 5-HT2A Binding:

Human recombinant serotonin 5-HT$_{2A}$ receptors expressed in CHO-K1 cells are used in modified Tris-HCl buffer pH 7.4. A 30 μg aliquot is incubated with 0.5 nM [3H]Ketanserin for 60 minutes at 25° C. Nonspecific binding is estimated in the presence of 1 μM Mianserin.Receptors are filtered and washed, the filters are then counted to determine [3H]Ketanserin specifically bound. Compounds, dissolved in DMSO, are screened at a concentration range between 3 nM and 30 μM. In previous studies, the maximal binding capacity of [3H]Ketanserin (Bmax) and its Kd were determined and amount to 510 fmol/mg protein and 0.2 nM, respectively.

Data Evaluation:

IC$_{50}$ values and Hill coefficient (nH) were determined by a non-linear, least squares regression analysis using MathIQ™ (ID Business Solutions Ltd., UK). The Ki values were calculated using the equation of Cheng and Prusoff (Biochem. Pharmacol. 22:3099-3108, 1973) using the observed IC$_{50}$ of the tested compound, the concentration of radioligand employed in the assay, and the historical values for the KD of the ligand (as determined previously).

Results:

The binding data for the examples of the current embodiment are summarized in FIG. 5.

Serotonin-Mediated Inositol Phosphate Response

The 5-HT2 receptor class couples preferentially to Gq/G11 to increase hydrolysis of inositol phosphates and elevate cytosolic [Ca$^{2+}$]. Human recombinant serotonin 5-HT$_{2A}$ receptor stably expressed in CHO-K1 cells are used. Test compound and/or vehicle is incubated with the cells (5×105/ml) in stimulation buffer of IP1 Tb kit (Cisbio Bioassays) for 30 minutes at 37° C. Test compound-induced increase of fluorescence relative to the 10 μM serotonin response indicate possible serotonin 5-HT$_{2A}$ receptor agonist activity. Test compound-induced inhibition of 0.3 μM serotonin-induced fluorescence response indicated receptor antagonist activity. EXAMPLE 1, EXAMPLE 1C and EXAMPLE 1D are screened at 1 μM demonstrated no agonist activity but antagonism of inhibition of 0.3 μM serotonin-induced fluorescence response by 30% and 37%, respectively.

Electrophysiology

Effects on Human Na$_V$1.1, Na$_V$1.2, Na$_V$1.3, Na$_V$1.4, Na$_V$1.5, Na$_V$1.6, Na$_V$1.7 and Na$_V$1.8/β3 Sodium Channels Expressed in Mammalian Cells CHO cells were stably transfected with human ion channel cDNAs. Stable transfectants were selected by expression with the antibiotic-resistance gene(s) incorporated into the expression plasmid(s). Selection pressure was maintained by including selection antibiotics in the culture medium. CHO cells were cultured in Ham's F-12 supplemented with 10% fetal bovine serum, 100 U/mL penicillin G sodium, 100 μg/mL streptomycin sulfate and appropriate selection antibiotics. Before testing, cells in culture dishes were washed twice with Hank's Balanced Salt Solution (HB-PS) and treated with Accutase for approximately 20 minutes. Immediately before use in IonWorks Barracuda™, the cells were washed in HB-PS to remove the Accutase and re-suspended in HB-PS. All experiments were performed at ambient temperature. Test articles and reference compound (lidocaine) concentrations were applied to naïve cells (n=4, where n=the number of replicate wells/concentration) via 384-channel pipettor. Duration of exposure to each test article concentration was five (5) minutes. Inhibition of Na$_V$ channels was measured using a stimulus voltage pattern. The pulse pattern was repeated before (baseline) and for five (5) minutes after compound addition. Peak current amplitudes were measured for test pulses TP1 (inactivated state inhibition), TP2, TP3 (tonic inhibition) and TP22 (use-dependent inhibition).

Concentration-response data were fit to an equation of the following form:

% Block=(100%)/[1+([C]/IC50)$^N$], where [C] was the concentration of test article, IC50 was the concentration of the test article producing half-maximal inhibition, N was the Hill coefficient, % VC was the percentage of the current run-down (the mean current inhibition at the vehicle control) and % Block was the percentage of ion channel current inhibited at each concentration of a test article. Nonlinear least squares fits were solved with the XLfit add-in for Excel (Microsoft, Redmond, Wash.). IC50 values of block for each Na$_V$1.x channel with the test article are presented in the Table below:

| | | EXAMPLE 1C IC$_{50}$, μM | | EXAMPLE 1D IC$_{50}$, μM | | EXAMPLE 1E IC$_{50}$, μM | | Lidocaine IC$_{50}$, μM | |
|---|---|---|---|---|---|---|---|---|---|
| | Channels | TP1 (tonic) | TP2 (inactivated state) | TP1 (tonic) | TP2 (inactivated state) | TP1 (tonic) | TP2 (inactivated state) | TP1 (tonic) | TP2 (inactivated state) |
| 1 | Na$_v$1.1 | >30 | 2.1 | >30 | 2.2 | >30 | 1.5 | 543.2 | 464.9 |
| 2 | Na$_v$1.2 | >30 | 3.1 | >30 | 2.1 | >30 | 1.5 | 496.4 | 410.9 |
| 3 | Na$_v$1.3 | >30 | 2.2 | >30 | 2.0 | >30 | 1.3 | 554.7 | 164.6 |
| 4 | Na$_v$1.4 | >30 | 1.5 | >30 | 1.3 | >30 | 1.2 | 389.2 | 162.1 |
| 5 | Na$_v$1.5 | >30 | 1.5 | >30 | 2.0 | >30 | 1.2 | 381.1 | 27.0 |
| 6 | Na$_v$1.6 | >30 | 2.2 | >30 | 2.0 | >30 | 1.2 | 422.7 | 187.6 |
| 7 | Na$_v$1.7 | >30 | 2.5 | >30 | 2.0 | >30 | 1.3 | 381.6 | 153.5 |
| 8 | Na$_v$1.8 | >30 | 1.9 | >30 | 1.8 | >30 | 1.1 | 279.8 | 51.4 |

Both EXAMPLE 1C, EXAMPLE 1D, and EXAMPLE 1E showed inhibition to Na$_V$1.1 to Na$_V$1.8 and were more than 10 to 100 times more potent than Lidocaine in blocking the inactivated state of the channels.

Those skilled in the art will appreciate that the invention described herein is susceptible to variations and modifications other than those specifically described. The present invention includes all such variations and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons for conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purposes of exemplification only. Functionally equivalent products, formulations and methods are clearly within the scope of the invention as described herein.

The invention described herein may include one or more ranges of values (e.g. concentration). A range of values will be understood to include all values within the range, including the values defining the range, and values adjacent to the range which lead to the same or substantially the same outcome as the values immediately adjacent to that value which defines the boundary to the range.

Throughout the specification, unless the context requires otherwise, the word "comprise" or variations such as "comprises" or "comprising", will be understood to imply the inclusion of a stated integer or group of integers but not the exclusion of other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

While the invention has been described with references to specific methods and embodiments, it will be appreciated that various modifications and changes may be made without departing from the invention.

REFERENCES

1. Soretti A and Fabbri C, 2013. "*Shared genetics among major psychiatric disorders.*" Lancet 381 (9875): 1339-1341.
2. Waszkielewicz A M, Gunia A, Szkaradek N, Sloczyńska K S, S. Krupinska S, Marona A (2013). "*Ion channels as drug targets in central nervous system disorders.*" Curr Med Chem 20, 1241-1285.
3. Roger S, Potier M, Vandier C, Besson P and Le Guennec J Y (2006). "*Voltage-gated sodium channels: new targets in cancer therapy?*" Curr Pharm Des 12(28): 3681-3695
4. Li M and Xiong Z G (2011). "*Ion channels as targets for cancer therapy.*" Int J Physiol Pathophysiol Pharmacol 2011, 3(2):156-166
5. Eijkelkamp N, Linley J E, Baker D M, Minett M S, Cregg R, Werdehausen R, Rugiero F and Wood J N (2012). "*Neurological perspectives on voltage-gated Sodium channels.*" Brain 135: 2585-2612.
6. Steers W D (2002). "*Pathophysiology of overactive bladder and urge urinary incontinence.*" Rev Urol 4 (Suppl4):S7-S18.
7. Zuliani V, Fantini M, Rivara M (2012). "*Sodium channel blockers as therapeutic target for treating epilepsy: recent updates.*" Curr Top Med Chem 12(9):962-70.
8. Davies H. M. L. et al. (2004). "*Synthesis of methylphenidate analogues and their binding affinities at dopamine and serotonin transport sites.*" Bioorg Med Chem Lett, 2004, 14, 1799-1802.

The invention claimed is:

1. A method for preparing and isolating a compound of formula (1):

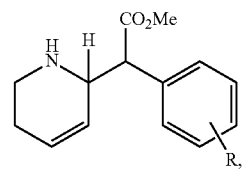

(1)

wherein R is selected from a group consisting of hydrogen, alkyl, alkenyl, alkoxy, halo, nitro, cyano, keto, amino, carboxylate, substituted or unsubstituted phenyls, adjacent rings which share a side with the R-bearing group, and a combination thereof, the method comprising the steps of:
a. reacting an aryldiazoacetate with a tetrahydropyridine having a nitrogen protecting group, in the presence of a non-chiral rhodium catalyst, wherein the non-chiral rhodium catalyst is a rhodium (II) octanoate dimer;
b. removing the protecting group; and
c. purifying and isolating threo- and erythro-diastereomers of the compound, wherein the purifying and isolating substantially removes the non-chiral rhodium catalyst.

2. The method of claim 1, the method further comprising the step of treating the erythro-diastereomer of the compound to obtain erythro-enantiomers of the compound.

3. The method of claim 1, further comprising the step of treating the threo-diastereomer of the compound to obtain threo-enantiomers of the compound.

* * * * *